(12) United States Patent
Raiszadeh

(10) Patent No.: US 8,454,657 B2
(45) Date of Patent: Jun. 4, 2013

(54) MEDICAL SYSTEMS FOR THE SPINE AND RELATED METHODS

(75) Inventor: Kamshad Raiszadeh, Rancho Santa Fe, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1950 days.

(21) Appl. No.: 10/881,155

(22) Filed: Jun. 30, 2004

(65) Prior Publication Data

US 2005/0277929 A1 Dec. 15, 2005

Related U.S. Application Data

(60) Provisional application No. 60/579,965, filed on Jun. 15, 2004.

(51) Int. Cl.
*A61B 17/70* (2006.01)
(52) U.S. Cl.
USPC .......................................... 606/246

(58) Field of Classification Search
USPC ................. 606/61, 301, 305, 74; 403/6, 179, 403/188, 347; 411/530
See application file for complete search history.

(56) References Cited

U.S. PATENT DOCUMENTS

| | | | | |
|---|---|---|---|---|
| 4,635,953 | A | * | 1/1987 | Robertson et al. ............ 280/480 |
| 6,277,120 | B1 | | 8/2001 | Lawson |
| 6,508,819 | B1 | * | 1/2003 | Orbay ............................. 606/69 |
| 6,520,965 | B2 | | 2/2003 | Chervitz et al. |
| 6,641,584 | B2 | | 11/2003 | Hashimoto et al. |
| 6,716,216 | B1 | * | 4/2004 | Boucher et al. ................. 606/86 |
| 2002/0040222 | A1 | * | 4/2002 | Hashimoto et al. ............. 606/61 |

* cited by examiner

*Primary Examiner* — Eduardo C Robert
*Assistant Examiner* — David Comstock

(57) ABSTRACT

Systems, methods, and kits for treating vertebras of a spine are disclosed. In some embodiments, an implantable medical system for treating vertebras of a spine includes a bone anchor configured to be secured to a vertebra, a wire, and a first elongated member configured to be attached to the bone anchor and the wire. The systems, methods, and kits can be used, for example, to treat C1 and C2 vertebras.

27 Claims, 3 Drawing Sheets

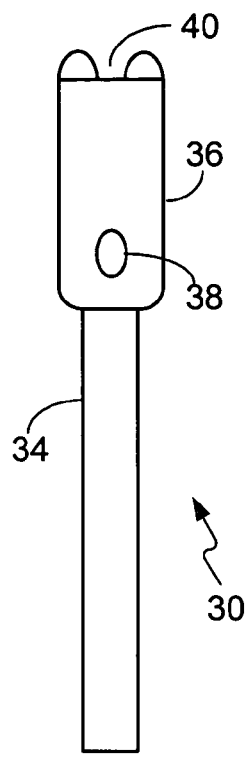 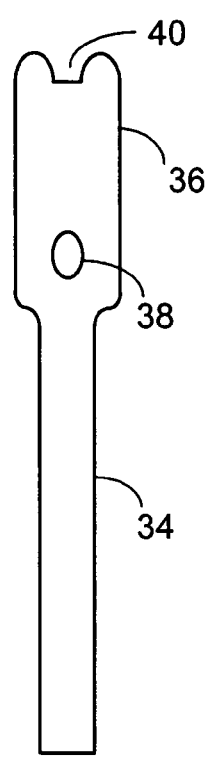 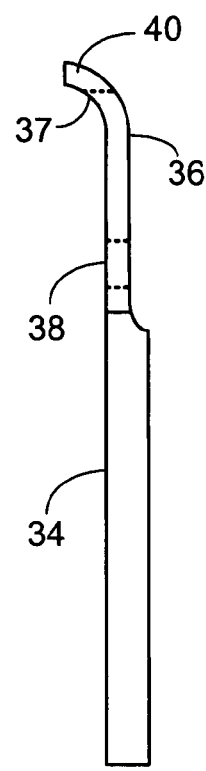
FIG. 3A   FIG. 3B   FIG. 3C
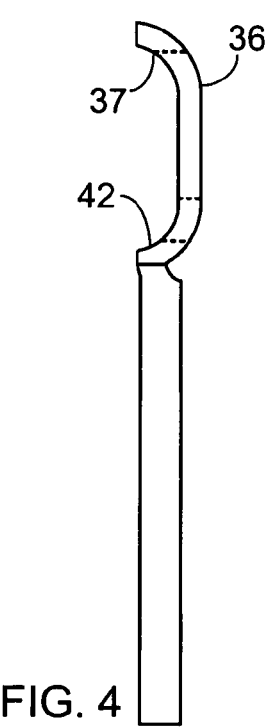 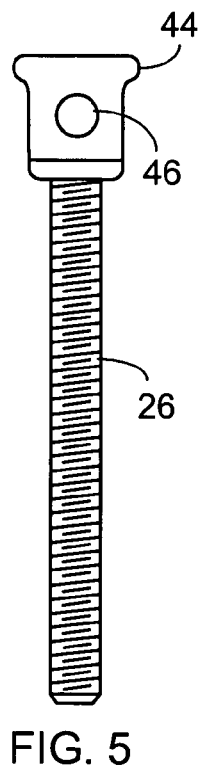 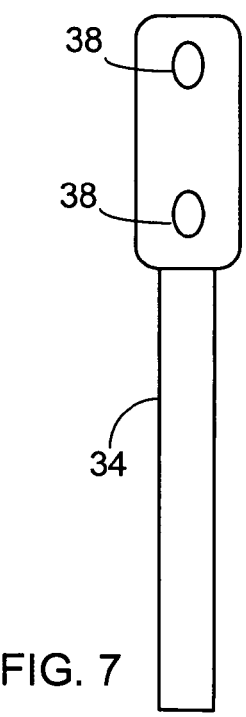
FIG. 4   FIG. 5   FIG. 7

MEDICAL SYSTEMS FOR THE SPINE AND RELATED METHODS

CLAIM OF PRIORITY

This application claims priority under 35 USC §119(e) to U.S. Provisional Patent Application Ser. No. 60/579,965, filed on Jun. 15, 2004, the entire contents of which are hereby incorporated by reference.

TECHNICAL FIELD

The invention relates to medical systems for treating the spine, and related methods.

BACKGROUND

The human spine includes a series of vertebras nominally divided up into sections by form and function. Starting from the top of the spine, the sections include the cervical vertebras, the thoracic vertebras, the lumbar vertebras, the sacral, and the coccyx. The cervical (neck) vertebras, for example, include the top seven vertebras that support the head. The topmost vertebra is C1 (or C-1), followed by C2. The lowest vertebra of the cervical vertebras is C7.

Sometimes, the joint between the vertebras can become unstable, for example, due to trauma, rheumatoid arthritis, or a tumor. The instability can be treated by techniques known as spinal fixation in which surgical implants mechanically immobilize selected vertebras, and allow the treated vertebras to fuse and to stabilize.

SUMMARY

In one aspect, the invention features medical systems, medical kits, and methods for treating the spine. The systems, kits, and methods can be used to treat adjacent vertebras, such as the commonly injured C1 and C2 vertebras.

In some embodiments, a medical system includes a bone anchor (such as a pedicle screw), a wire, and an elongated first member configured to be attached to the bone anchor and to the wire. For example, the bone anchor can be attached to a pedicle (also called "pars") of a C2 vertebra, and the wire can be attached to a C1 vertebra (such as by wrapping the wire around the lamina of the vertebra). The elongated first member can be connected to both the anchor and the (sublaminar) wire to stabilize the vertebras, thereby allowing the vertebras to fuse. The medical system is capable of providing the vertebras with good biomechanical stability without the need, for example, to embed an anchor (such as a screw) in the C1 vertebra, which can be difficult and dangerous because multiple vital structures (such as the vertebral artery, the spinal cord, and the exiting nerve root) pass near or through these vertebras.

In another aspect, the invention features an implantable medical system for treating vertebras of a spine, including a bone anchor configured to be secured to a vertebra; a wire; and an elongated first member configured to be attached to the bone anchor and the wire.

In another aspect, the invention features an implantable medical system for treating vertebras of a spine, including a pedicle screw; a wire; and an elongated first member having a first portion configured to connect to the screw, and a second portion configured to contact a vertebra and to connect to the wire.

In yet another aspect, the invention features a method of treating vertebras of a spine, including securing a wire to a first vertebra; securing a bone anchor to a second vertebra; and securing an elongated first member to the bone anchor and to the wire.

In another aspect, the invention features a method of treating vertebras of a spine, including securing a first wire to a first vertebra; securing a first anchor to a second vertebra adjacent to the first vertebra; and securing an elongated first member to the first wire and to the first anchor, the first member comprising a first portion that contacts the first vertebra.

In another aspect, the invention features a method of treating a C1 vertebra and a C2 vertebra, including securing a first wire to the C1 vertebra; securing a first anchor to the C2 vertebra; and connecting the first wire to the first anchor.

In another aspect, the invention features a kit for treating vertebras of a spine, including a first bone anchor; a first wire; and an elongated first member configured to be attached to the bone anchor and to the wire.

In another aspect, the invention features a method of treating a first vertebra and a second vertebra, including connecting the first vertebra to the second vertebra with an elongated first member, wherein a portion of the first member contacts the first vertebra.

In another aspect, the invention features a method of treating a first vertebra and a second vertebra, including extending an elongated member around a portion of the first vertebra; embedding an anchor into the second vertebra; and connecting the elongated member to the anchor.

Other aspects, features and advantages of the invention will be apparent from the description of the preferred embodiments thereof and from the claims.

BRIEF DESCRIPTION OF DRAWINGS

FIG. 3A is an anterior view of an embodiment of an elongated member; FIG. 3B is a posterior view of the member of FIG. 3A; and FIG. 3C is a lateral view of the member of FIG. 3A.

FIG. 4 is a lateral view of an embodiment of an elongated member.

FIG. 5 is a lateral view of an embodiment of a screw.

FIG. 7 is a posterior view of an embodiment of an elongated member.

DETAILED DESCRIPTION OF THE PREFERRED EMBODIMENTS

Figure 1:
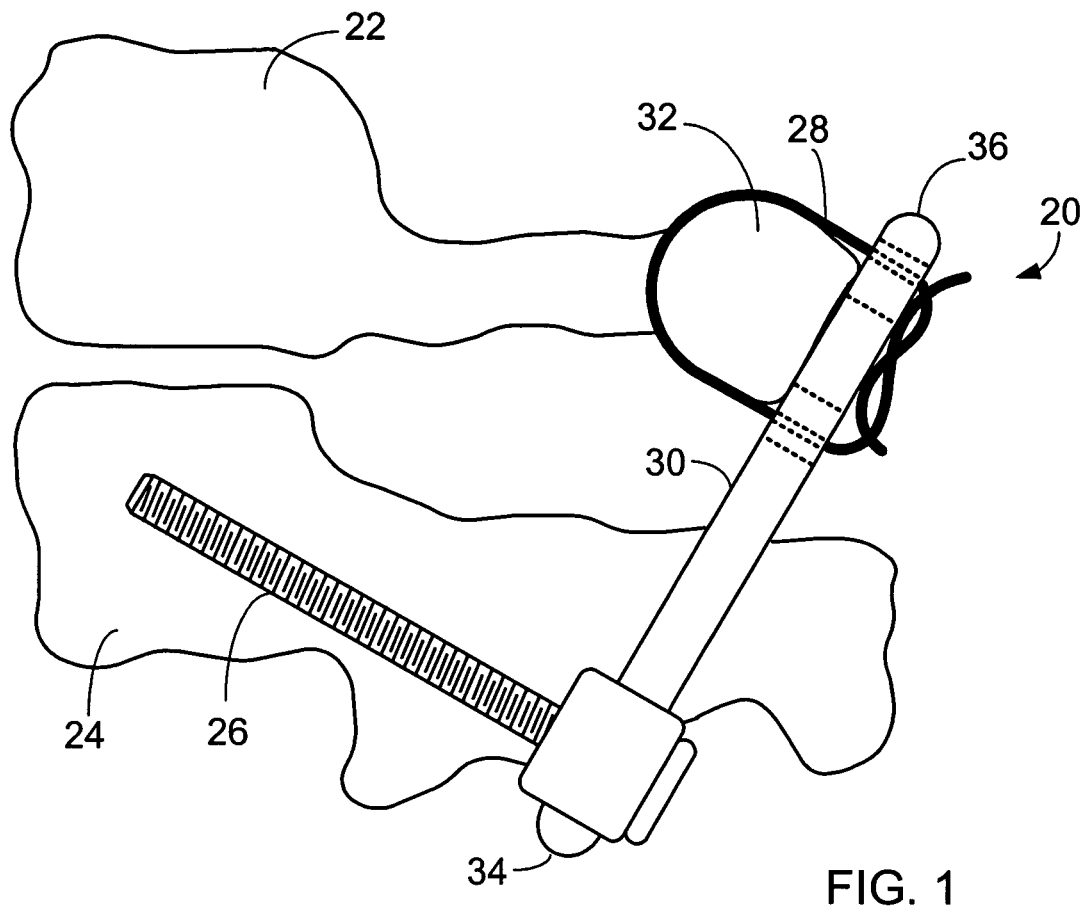
FIG. 1 is a lateral view of an embodiment of an implantable medical system.
Figure 2:
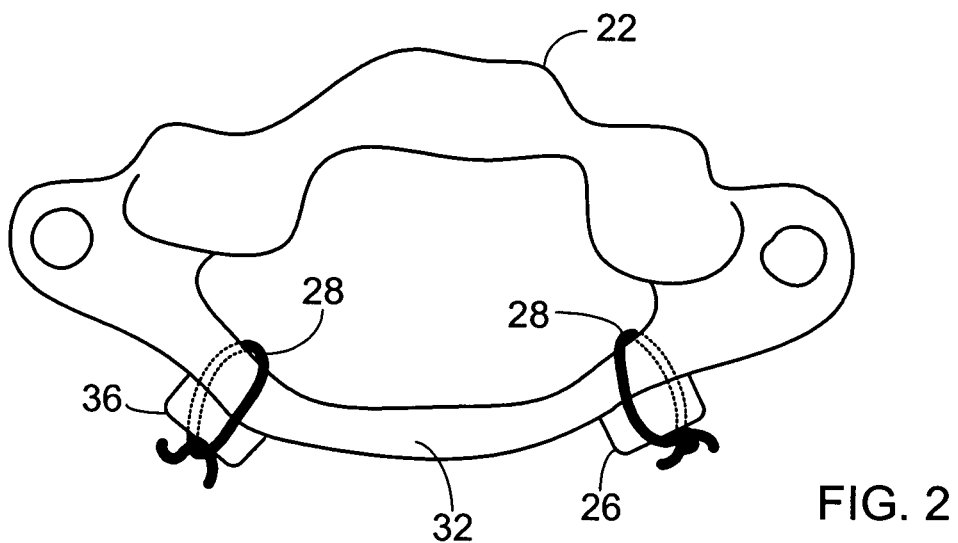
FIG. 2 is a top view of a C1 vertebra and a portion of the medical system of FIG. 1.

Referring to FIGS. 1 and 2, two medical systems 20 are implanted to a C1 vertebra 22 and a C2 vertebra 24 (although for clarity, only one medical system is shown in FIG. 1). Each medical system 20 includes a bone anchor (as shown, a pedicle screw 26), a wire 28, and an elongated member 30 configured to be connected to the bone anchor and the wire. As shown, pedicle screw 26 is secured to a pedicle of C2 vertebra 24, and wire 28 is secured to C1 vertebra 22 by wrapping the wire around a portion of a lamina 32 (or posterior arch) of the C1 vertebra. Elongated member 30 is secured to pedicle screw 26 and to wire 28. Medical systems 20 are capable of providing biomechanical stability to vertebras 22 and 24, whose joints may have destabilized due to an injury or a medical condition, so that the vertebras can fuse together to reduce the instability. In addition, systems 20 are capable of providing stability without the need to place a screw into C1 vertebra 22 or using a transarticular screw, both of which can involve difficult or dangerous procedures.

Referring to FIGS. 3A-3C, in addition to being configured to be connected to screw 26 and wire 28, elongated member 30 is configured to interface with C1 vertebra 22. Elongated member 30 includes a plate-like portion 36 and an elongated portion (as shown, cylindrical portion 34) connected to the plate-like portion. Plate-like portion 36 includes a curved portion 37 and defines an opening 38 and a notch 40, which is located at an end of elongated member 30. The curvature of portion 37 is similar to the curvature of lamina 32 of C1 vertebra 22 to provide good contact as described below. In some embodiments, the anterior side (as shown, the side that contacts lamina 32) of plate-like portion 36 is roughened or textured to enhance friction between the plate-like portion and the lamina and to reduce movement or slippage of member 30 after implantation. For example, the anterior side can include ridges, grooves, bumps, and/or other protrusions. Alternatively or additionally, the anterior side can be coated with one or more bone-forming materials, such as hydroxyapetite. Alternatively or additionally, referring to FIG. 4, in some embodiments, plate-like portion 36 can also include a second curved portion 42 to more closely match the curvature of lamina 32. Opening 38 and notch 40 are sized to receive and to engage with wire 28, respectively. Cylindrical portion 34 is configured to engage with anchor 26, e.g., by being sized to be received into an opening defined by screw 26 (described below). Cylindrical portion 34 can be solid or hollow (e.g., defining a lumen).

Wire 28 can be formed of any biocompatible and malleable material capable of being used for orthopedic implantations. Examples of materials include metals, such as stainless steel and titanium. In some embodiments, wire 28 can be a filament having a diameter from about one to about 1.5 mm. In other embodiments, wire 28 can have the shape of a ribbon or a band. Opening 38 and notch 40 can be configured to receive and to engage with the ribbon or the band.

Similarly, anchor 26 can be formed of any biocompatible and rigid material capable of being used for orthopedic implantations. As shown in FIG. 1, anchor 26 can be a screw, such as a 2.5 to 3.5 mm polyaxial pedicle screw. Referring to FIG. 5, screw 26 can have a head portion 44 defining an opening 46 through which cylindrical portion 34 of elongated member 30 can be passed. Anchor 26 can be manufactured from, for example, stainless steel and/or titanium.

In use, the components of one or more medical systems 20 (such as screw 26, wire 28, and elongated member 30) can be provided in a kit prior to implantation.

During implantation, screw 26 is secured to C2 vertebra 24, wire 28 is placed on lamina 32 C1 vertebra 22, and the screw and the wire are secured together. More specifically, a posterior approach is made to subperiosteally dissect the muscles off of the posterior arch of C2 vertebra 24 and lamina 32 of C1 vertebra 22. Two screws 26 are then placed into the pedicles or pars of C2 vertebra 24, for example, by using bony landmarks of the C2 vertebra to drill, tap, and place the screws. Next, two wires 28 (one on each side of the midline of the vertebras) are passed under lamina 32 of C1 vertebra 22. Wires 28 can be placed anywhere between the midline and the edge of lamina 32, for example, about 1 to about 1.5 cm off of the midline.

With screws 26 and wires 28 in place, two elongated members 30 are prepared and then implanted. Members 30 can first be sized and cut to length. The cylindrical portion 34 of the first elongated member 30 is then lowered into opening 46 of one of the screws 26 (the first screw). The wire 28 cephalad to the first screw is then passed through opening 38 of plate-like portion 36 of the first elongated member 30, which is then positioned (e.g., lowered) so that the plate-like portion contacts lamina 32 of C1 vertebra 22. Wire 28 is then secured to the first elongated member 30. For example, if the wire 28 includes a malleable material (such as stainless steel), the wire can be fitted into notch 40 and twisted on the posterior side of plate-like portion 36 to secure the wire to elongated member 30. For less malleable or brittle materials (such as titanium), wire 28 can be secured using a crimped metal band (such as Songer). Cylindrical portion 34 of the first elongated member 30 is then secured to first screw 26, for example, by tightening a setscrew on the first screw. The second elongated member 30 can be secured to the other wire and screw using the same procedures described above. In some embodiments, some compression can be applied to medical systems 20 prior to final tightening. Bone graft material (such as iliac bone graft, the patient's own local bone, and/or allograft and/or synthetic bone substitute) can be placed around medical systems 20.

Figure 6:
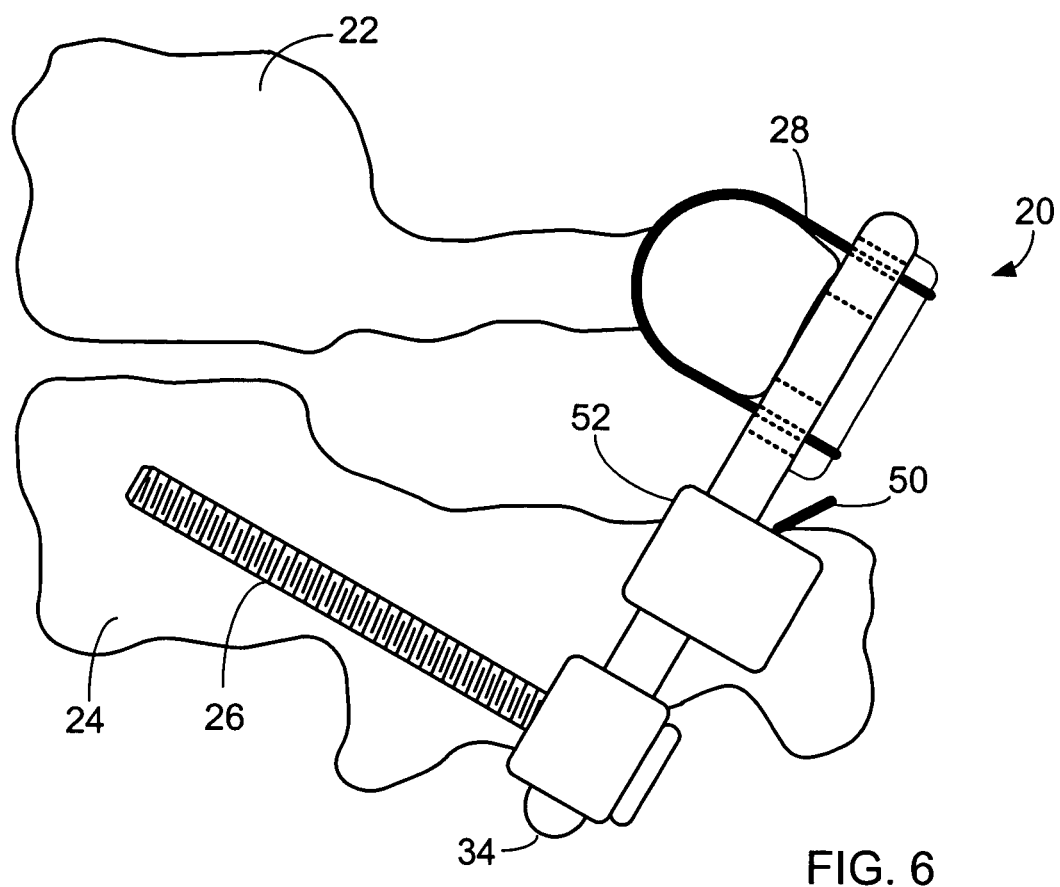
FIG. 6 is a lateral view of an embodiment of an implantable medical system.

In some embodiments, the two elongated members 30 can be connected together to enhance stability. For example, referring to FIG. 6, the two elongated members 30 can be joined together using an elongated cross connector 50 (such as a rod-like member) that attaches transversely to the members 30, for example, using two joints 52 that slidably receives the members 30.

Additionally, while the methods described above can be used for a bilateral implant, in other embodiments, only one medical system 20 can be implanted, for example, when only one pedicle is available.

While a number of embodiments have been described, the invention is not so limited. For example, while the systems and methods described above refer to C1 and C2 vertebras, in other embodiments, the systems and methods can be used to treat other vertebras.

As another example, plate-like portion 36 can include multiple openings. For example, referring to FIG. 7, plate-like portion 36 can include two openings 38 through which wire 28 can be passed, e.g., rather than having an opening and notch 40.

Other embodiments of cylindrical portion 34 can be used. For example, the elongated portion of member 30 can have a cross section that is non-circular, such as oval, elliptical, regularly or irregularly polygonal, having three, four, five, six, seven, eight or more sides.

All references, such as patents, patent applications, and publications, referred to above are incorporated by reference in their entirety.

Other embodiments are within the scope of the following claims.

What is claimed is:
1. An implantable medical system for treating vertebras of a spine, comprising:
   a bone anchor configured to be secured to a first vertebra, the bone anchor comprising a head portion including an opening;
   a wire; and
   an elongated first member extending along an axis between a first end and a second end, the first end including an opening extending transverse to the axis through the first end having the wire disposed therein, the second end being positioned at the bone anchor, wherein the wire secures the first end of the elongated first member to a second vertebra, the first member sized to engage the opening and including a length with the wire spaced apart from the bone anchor to connect the first vertebra to the second vertebra.

2. The system of claim 1, wherein the elongated first member comprises a first portion configured to contact a portion of a vertebra.

3. The system of claim 2, wherein the elongated first member includes the first portion and a second portion positioned in an end-to-end arrangement, the first portion is a plate that is configured to contact a lamina of a C1 vertebra and includes a greater width than the second portion.

4. The system of claim 2, wherein the first portion includes a distal section that is curved and a planar proximal section, the distal section including a smaller length than the planar proximal section measured along a longitudinal axis of the first member.

5. The system of claim 2, wherein the first portion comprises two curved portions that are spaced apart by an intermediate planar section.

6. The system of claim 2, wherein the opening in the elongated first member extends through the first portion.

7. The system of claim 6, wherein the first portion defines a notch at a distal end with the notch being centered along the axis.

8. The system of claim 2, wherein the first portion is textured.

9. The system of claim 1, wherein the elongated first member comprises an elongated cylindrical portion and a first portion connected to the elongated cylindrical portion, the first portion being configured to contact a portion of a vertebra and includes a greater width than the elongated cylindrical portion.

10. The system of claim 9, wherein the first portion is curved.

11. The system of claim 9, wherein the opening in the elongated first member extends through the first portion and a notch and the opening in the elongated first member are each positioned along the axis.

12. The system of claim 1, wherein the bone anchor comprises a screw.

13. The system of claim 1, wherein the wire comprises titanium or stainless steel.

14. The system of claim 1, further comprising an elongated second member configured to be attached to the elongated first member.

15. An implantable medical system for treating vertebras of a spine, comprising:
a pedicle screw comprising a head portion including an opening;
a wire; and
an elongated first member extending along an axis between a first portion and a second portion, the first portion including an opening extending transverse to the axis through the first portion having the wire disposed therein, the second portion being positioned in the opening in the head portion, the first portion including a plate with a width greater than the second portion to contact a vertebra, the elongated first member having a length with the wire and the plate both spaced away from the opening of the pedicle screw.

16. The system of claim 15, wherein the first portion is curved at a distal end away from the second portion.

17. The system of claim 15, wherein the first portion defines a notch positioned at a distal end of the first portion away from the second portion.

18. The system of claim 15, wherein the plate includes a contact surface that is textured to contact the vertebra.

19. The system of claim 15, wherein the second portion includes a straight shape and is slidably received by the screw.

20. The system of claim 15, further comprising an elongated second member configured to connect to the elongated first member.

21. A kit for treating vertebras of a spine, comprising:
a first bone anchor comprising a head portion including an opening;
a first wire; and
an elongated first member extending along an axis between a first end and a second end, the first end being movably attached to the bone anchor and the second end including an opening extending transverse to the axis through the second end configured for disposal of the wire;
the opening in the head portion being sized to accept the first end therein and allow the first member to move within the opening in the head portion;
the first member including a length measured between the first and second ends that spaces the wire away from the first bone anchor.

22. The kit of claim 21, wherein the bone anchor is a pedicle screw.

23. The kit of claim 21, wherein first member comprises an elongated portion with a cylindrical cross-sectional shape connected to a plate with a curved first portion, the plate including a greater width than the elongated portion.

24. The kit of claim 23, wherein the curved first portion defines the opening in the second end and a notch.

25. The kit of claim 21, further comprising a second bone anchor, a second wire, and an elongated second member configured to be attached to the second bone anchor and to the second wire.

26. The kit of claim 25, further comprising an elongated third member configured to be attached to the first member and to the second member.

27. The kit of claim 21, further comprising instructions for treating C1 and C2 vertebras.

* * * * *